United States Patent [19]

Mueller et al.

[11] 4,363,924

[45] Dec. 14, 1982

[54] DEPOLYMERIZATION OF POLYTETRAMETHYLENE GLYCOL ETHERS

[75] Inventors: Herbert Mueller, Frankenthal; Otto H. Huchler, Limburgerhof, both of Fed. Rep. of Germany

[73] Assignee: BASF Aktiengesellschaft, Ludwigshafen, Fed. Rep. of Germany

[21] Appl. No.: 313,657

[22] Filed: Oct. 22, 1981

[30] Foreign Application Priority Data

Nov. 14, 1980 [DE] Fed. Rep. of Germany ....... 3042960

[51] Int. Cl.$^3$ ........................................... C07D 307/08
[52] U.S. Cl. ................................................. 549/509
[58] Field of Search .................... 260/346.11; 549/509

[56] References Cited

U.S. PATENT DOCUMENTS

| | | | |
|---|---|---|---|
| 2,751,419 | 6/1956 | Hill et al. | 260/346.11 X |
| 3,433,829 | 3/1969 | Dörfelt | 560/240 |
| 3,925,484 | 12/1975 | Baker | 260/346.11 |
| 4,115,408 | 9/1978 | Baker | 260/346.11 |
| 4,233,228 | 11/1980 | Mueller et al. | 260/346.11 |

FOREIGN PATENT DOCUMENTS 6104881 8/1981 Japan ................................ 549/509

OTHER PUBLICATIONS

Davis, Makromol. Chem., vol. 81, (1965), pp. 38–50.

*Primary Examiner*—Richard Raymond
*Attorney, Agent, or Firm*—John H. Shurtleff

[57] ABSTRACT

A process for depolymerizing polytetramethylene glycol ethers, wherein the latter are heated at from 90° to 180° C. in the presence of a bleaching earth.

6 Claims, No Drawings

DEPOLYMERIZATION OF POLYTETRAMETHYLENE GLYCOL ETHERS

The present invention relates to a process for depolymerizing polytetramethylene glycol ethers.

Polytetramethylene glycol ethers, which are used as high-quality polymeric glycols for the preparation of polyurethane resins, are obtained by polymerizing tetrahydrofuran. In general, the polymerization products are required to have molecular weights of from 500 to 3,000.

If the apparatus used to prepare the polytetrahydrofuran is changed over from settings corresponding to a particular molecular weight to settings which give a different molecular weight, product mixing occurs, giving off-specification fractions composed of polymers of different molecular weight ranges. In order to find an economically acceptable use for this off-specification material, it is desirable, for example, to reconvert it to monomer, namely to tetrahydrofuran. This requirement also arises whenever uncontrolled events during the synthesis lead to polymers which do not conform to the required narrow specification.

In the preparation of polytetramethylene glycol ethers, the polymer is purified by aqueous extractive treatment, for example by the method of U.S. Pat. No. 2,751,419. The resulting effluent contains dissolved polytetramethylene glycol ethers and therefore has a very high chemical oxygen demand (COD) and pollutes the sewers. U.S. Pat. No. 4,115,408 describes a process for depolymerizing polytetramethylene glycol ethers to tetrahydrofuran, in which such effluent is heated with sulfuric acid at 150° C. This process has two disadvantages in particular. First, the use of relatively concentrated acid at 150° C. necessarily entails substantial corrosion problems, and, secondly, the dilute aqueous sulfuric acid obtained after the depolymerization must be neutralized before it can be discharged into the sewer, thereby imposing a substantial salt load on the sewer.

It has also been proposed to degrade polytetrahydrofuran by pyrolysis (Makromol. Chem. 81 (1965), 38–50). However, this method has the disadvantage that the decomposition follows more than one course, and a plurality of pyrolysis products are formed.

It is an object of the present invention to provide a process whereby polytetramethylene glycol ethers can be quantitatively reconverted to tetrahydrofuran by a simpler method, which also avoids polluting the environment with salt or acid.

We have found that this object is achieved if, according to the invention, the polytetramethylene glycol ethers are depolymerized by heating them at from 90° to 180° C., preferably 100° to 150° C., in the presence of a bleaching earth.

The process of the invention reconverts the polymer to the monomer in a particularly advantageous manner, and without loss of yield. Furthermore, the monomer obtained is of excellent purity and can therefore, after drying, be very successfully recycled—without further treatment—to the polymerization.

Bleaching earths suitable for carrying out the process according to the invention are naturally occurring hydrated aluminum hydrosilicates of the montmorillonite group; conventionally, these are in most cases subjected to an acid treatment, before use, in order to purify, digest and activate them.

Only a small amount of the bleaching earth is required for the depolymerization of the polytetramethylene glycol ethers. Advantageous results are achieved by using, for example, from 0.1 to 5%, based on polymer, of the bleaching earth. Of course, smaller or larger amounts can also be used. Advantageously, from 1 to 2% by weight is employed. Once the bleaching earth has been used, it can be re-used, as often as desired, for a fresh depolymerization.

To carry out the depolymerization process, the polymer is mixed with the bleaching earth and the mixture is heated to the reaction temperature. The reaction commences at about 90°–100° C., and at 100°–130° C. is sufficiently rapid to allow it to be carried out industrially. If, for example, 1% by weight of bleaching earth is added to the polymer and the reaction temperature is kept at 130° C., the depolymerization is complete after about 3–4 hours. The decomposition vessel no longer contains any organic substance, but only the inorganic catalyst employed. The latter can be used direct for a fresh batch. If higher temperatures or higher concentrations of bleaching earth are used, the reaction takes place more rapidly.

Because the catalyst employed can be re-used, the amount of catalyst employed is very small compared to the depolymerization of throughput. If, nevertheless, it is desired to discharge the catalyst, the latter can be safely dumped, being an inert, natural inorganic material.

The fact that polytetramethylene glycol ethers can be depolymerized with bleaching earths is very surprising, since it is known from U.S. Pat. No. 3,433,829 that treating tetrahydrofuran with bleaching earths at from 20° to 200° C. gives polytetrahydrofuran.

In the Example, parts are by weight.

EXAMPLE

A reaction vessel equipped with heating, a stirrer and a descending condenser is charged with 400 parts of polytetramethylene glycol ether of molecular weight 2,000 and 4 parts of TONSIL OPTIMUM FF and the mixture is then heated to 130° C., with stirring. TONSIL OPTIMUM FF is a commercial bleaching earth from Südchemie AG, Munich, having a bulk density of 450 g/l.

Elimination of tetrahydrofuran commences above 100° C. After 3 hours, 399–400 parts of tetrahydrofuran have been obtained in the receiver attached to the condenser. 4 parts of the bleaching earth powder remain, as the residue, in the stirred vessel. Analysis by gas chromatography does not show any impurities—other than small amounts of water originating from the bleaching earth employed and from the depolymerization—in the tetrahydrofuran obtained.

A further 2 charges each of 400 parts of polytetramethylene glycol ether, of molecular weight 1,000 and 650 respectively, are depolymerized with the anhydrous bleaching earth left in the stirred vessel. No reduction in the catalyst activity is found. These reactions also take place quantitatively.

We claim:

1. A process for depolymerizing polytetramethylene glycol ethers which comprises heating a polytetramethylene glycol ether in the presence of a bleaching earth at from 90° to 180° C.

2. A process as claimed in claim 1, wherein the mixture is heated at from 100° to 150° C.

3. A process as claimed in claim 1, wherein from 0.1 to 5 percent by weight, based on polytetramethylene glycol ether, of bleaching earth is used.

4. A process as claimed in claim 3 wherein the amount of bleaching earth used is about 1 to 2 percent by weight, based on polytetramethylene glycol ether.

5. A process as claimed in claims 1, 2 or 3 wherein the polytetramethylene glycol ether is heated in a reaction mixture substantially free of salt and acid.

6. A process as claimed in claims 1, 2 or 3 wherein said bleaching earth is an acid-treated aluminum hydrosilicate of the montmorillonite group.

* * * * *